United States Patent [19]

Fundingsland et al.

[11] Patent Number: 5,295,827
[45] Date of Patent: Mar. 22, 1994

[54] SYRINGE TIP FORMING APPARATUS

[75] Inventors: Jon W. Fundingsland, Stillwater; Ralph F. Rogers, Woodbury, both of Minn.

[73] Assignee: Minnesota Mining and Manufacturing Company, St. Paul, Minn.

[21] Appl. No.: 977,926

[22] Filed: Nov. 18, 1992

Related U.S. Application Data

[63] Continuation-in-part of Ser. No. 795,941, Nov. 18, 1991, abandoned.

[51] Int. Cl.$^5$ .............................................. A61G 17/02
[52] U.S. Cl. ................................... 433/80; 433/49; 433/77; 433/141; 433/229; 206/368
[58] Field of Search ................ 433/25, 49, 50, 77, 433/80, 81, 141, 229; 72/369, 462, 467, 468; 206/368, 369

[56] References Cited

U.S. PATENT DOCUMENTS

| | | | |
|---|---|---|---|
| 91,592 | 6/1869 | Ayres | 72/461 |
| 386,750 | 7/1888 | Kimball | 433/49 |
| 1,419,550 | 6/1922 | Fischer | 72/461 |
| 1,684,417 | 9/1928 | Silberman | 433/229 |
| 2,102,591 | 12/1937 | Hagemeier | 604/223 |
| 2,702,577 | 2/1955 | Harrison et al. | 72/467 |
| 2,824,475 | 2/1958 | Rolando | 72/457 |
| 3,488,849 | 1/1970 | Lieb et al. | 433/78 |
| 3,559,433 | 2/1971 | Brown et al. | 72/36 |
| 3,624,907 | 12/1971 | Brass et al. | 433/81 |
| 3,722,256 | 3/1973 | Iascone | 72/470 |
| 3,727,310 | 4/1973 | Baker | 433/80 |
| 3,745,655 | 7/1973 | Malmin | 433/81 |
| 3,807,048 | 4/1974 | Malmin | 433/81 |
| 3,816,921 | 6/1974 | Malmin | 433/81 |
| 3,919,875 | 11/1975 | Maev et al. | 72/369 |
| 4,109,383 | 8/1978 | Reed et al. | 433/72 |
| 4,184,251 | 1/1980 | Kuboki | 433/77 |
| 4,256,457 | 3/1981 | Behring | 433/77 |
| 4,265,618 | 5/1981 | Herskovitz et al. | 433/32 |
| 4,353,694 | 10/1982 | Pelerin | 433/77 |
| 4,751,840 | 6/1988 | Windsor, Jr. | 72/478 |
| 5,106,297 | 4/1992 | Discko | 433/77 |

Primary Examiner—John J. Wilson
Attorney, Agent, or Firm—Gary L. Griswold; Walter N. Kirn; James D. Christoff

[57] ABSTRACT

A forming apparatus has a passage with a chamfered entrance for bending a tip of a syringe such as a syringe used for dispensing dental material. The passage and chamfered entrance enable the tip to be bent to a desired angular configuration while in view of the user.

16 Claims, 5 Drawing Sheets

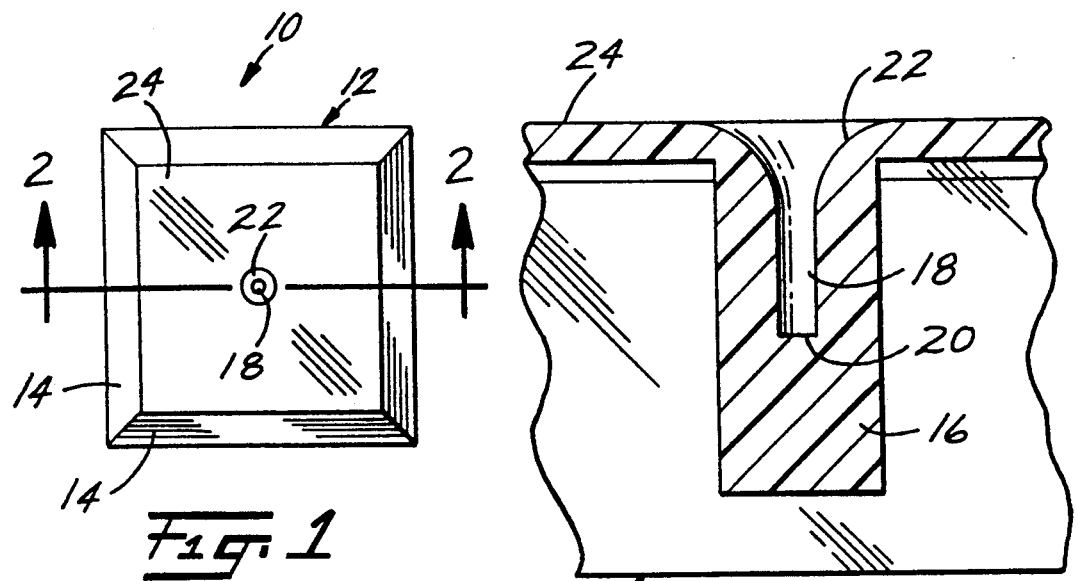
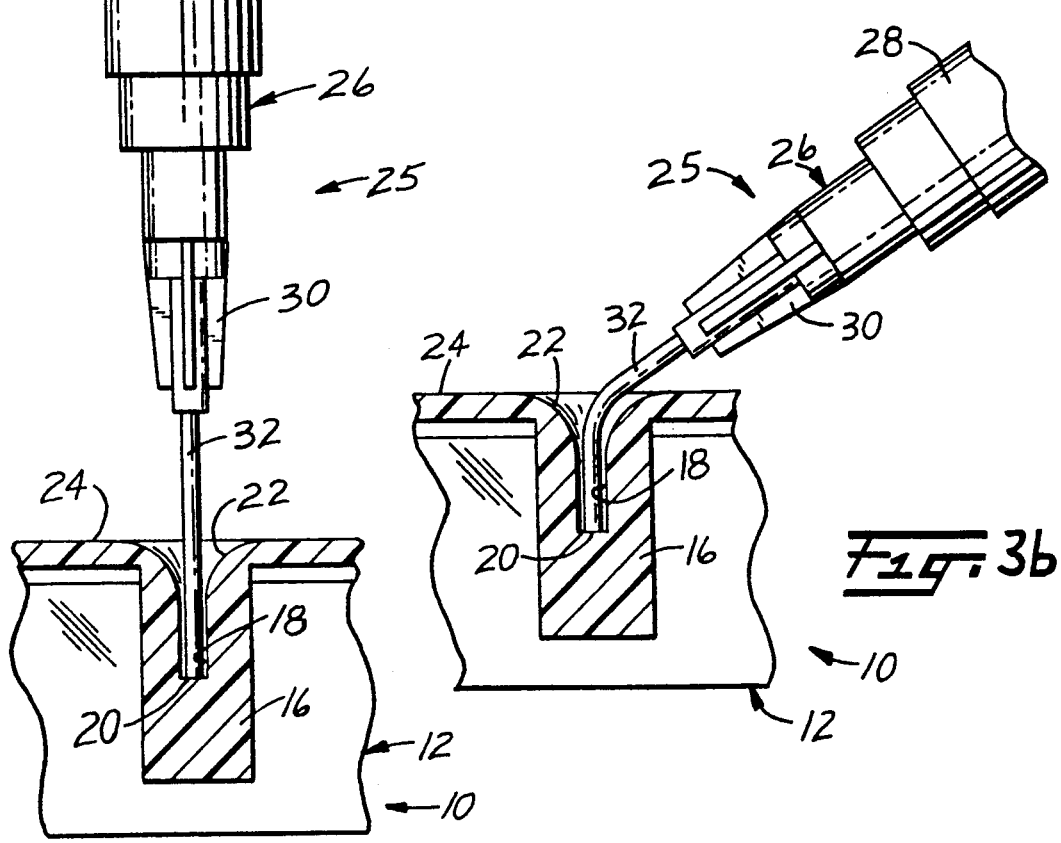

SYRINGE TIP FORMING APPARATUS

This application is a continuation-in-part of application Ser. No. 07/795,941 filed Nov. 18, 1991, now abandoned.

BACKGROUND OF THE INVENTION

1. Field of the Invention

This invention relates to apparatus for bending a tip of a dispensing syringe.

2. Description of the Related Art

Syringes are widely used in health care procedures and typically include a hollow barrel containing a quantity of fluid and a thumb-operated plunger for dispensing the fluid from the barrel through a hollow needle or tip. Syringe tips are often made of stainless steel tubing having a relatively small diameter.

The tip of a syringe normally extends in a straight direction along an axis that is colinear with the longitudinal axis of the barrel and the axis of movement of the plunger into the barrel. In some instances, however, it is desirable to bend the tip to an angle that provides more convenient dispensing of the fluid to a location that otherwise might be difficult to reach.

For example, dentists often use syringes that contain a quantity of etching gel for etching tooth enamel in order to enhance the subsequent bond of a dental adhesive to the enamel. However, certain types of etching gel contain phosphoric acid which may irritate the gingiva and other tissue in the mouth. Since access to portions of certain teeth is difficult, it is often desirable to bend the tip of the syringe in a curved arc to ensure that the etching gel is properly placed on the selected surface areas of tooth enamel without contacting adjacent tissue.

In the past, dental practitioners sometimes have attempted to bend the tips of syringes by holding the syringe barrel in one hand and forming the tip between the thumb and forefinger of the other hand. However, such a procedure is not entirely satisfactory because latex gloves worn by the practitioner may be punctured by the metal tip as the tip is bent. Moreover, it is sometimes difficult to bend the tip by hand at a certain location along its length and to precise angular configuration because the tip is relatively small and the thumb and forefinger may obscure the view of the bending operation.

SUMMARY OF THE INVENTION

The present invention in one embodiment is directed toward an assembly of a syringe having a formable tip with a diameter less than about 0.5 cm, and a syringe tip forming apparatus including a substrate having a passage with an effective diameter no greater than about 0.5 cm. The substrate includes a chamfered entrance connected to the passage. The chamfered entrance has a radius of at least two times the effective diameter.

In a second embodiment of the invention, a syringe tip forming apparatus comprises a dental mixing pad with a substrate having at least one well for mixing dental material. The substrate has a passage and a chamfered entrance connected to the passage. In another embodiment, the apparatus comprises a dental instrument setup tray having a bottom and a plurality of holders for holding dental instruments at a position spaced above the bottom; a passage and a chamfered entrance are connected to the tray. In another embodiment, the apparatus comprises a package which includes a first and second recess, and the package is part of an assembly that includes a container of dental material received in the first recess and a syringe received in the second recess; and a passage and a chamfered entrance are connected to the package.

BRIEF DESCRIPTION OF THE DRAWINGS

FIG. 1 is a plan view of the apparatus in accordance with one embodiment of the invention;

FIG. 2 is an enlarged, fragmentary, side cross-sectional view taken along lines 2—2 of FIG. 1;

FIG. 3a is a view somewhat similar to FIG. 2 in reduced form and additionally showing a tip of a syringe inserted in a passage of the apparatus;

FIG. 3b is a view somewhat similar to FIG. 3a except that the syringe has been moved in an arc in order to bend the tip;

DETAILED DESCRIPTION OF THE PREFERRED EMBODIMENTS

Figure 4:
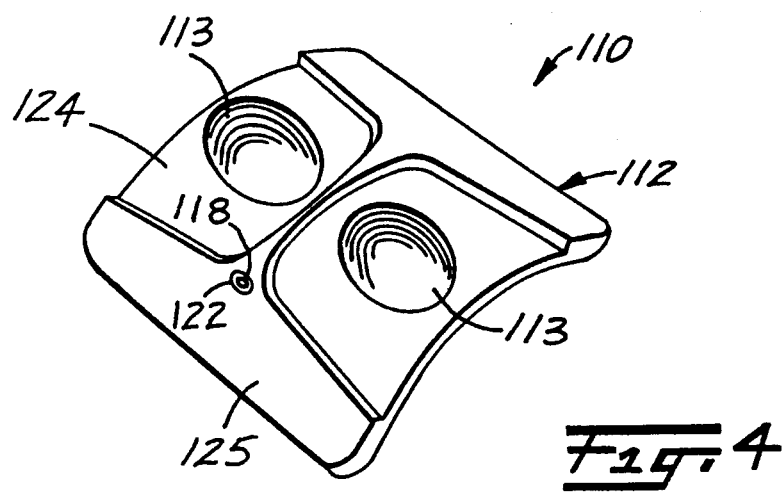
FIG. 4 is a perspective view of another embodiment of the invention, wherein a dental mixing well includes a passage for forming a syringe tip.

A syringe tip forming apparatus 10 is shown in FIGS. 1-3 and comprises a substrate 12 that is preferably made of metal or a relatively hard and clear synthetic resinous material such as acrylic, polypropylene or polycarbonate. The substrate 12 includes four beveled edges 14, and a depending body 16 that extends into a hollow interior of the substrate 12.

The body 16 has an elongated vertical passage 18 that terminates at a lower end 20. The passage 18 is essentially cylindrical, but preferably has a slight frustoconical taper in the range of 1 to 2 degrees to facilitate molding the body 16.

A trumpeted or chamfered entrance 22 is connected to the passage 18, and as shown in FIGS. 2-3 provides a smooth curved transition between the passage 18 and a top 24 of the substrate 12. The lowermost portion of the entrance 22 narrows to a diameter equaling the diameter of the passage 18. In cross-sectional view, the arc forming the entrance 22 is tangential at its uppermost end with the top 24, and is tangential at its lowermost end with the wall defining the passage 18.

The effective diameter of the passage 18 is no greater than about 0.5 cm, and is preferably no greater than about 0.1 cm. As used herein, the phrase "effective diameter" is a value equal to the diameter of the largest cylinder that can be placed in the passage 18. Thus, the passage 18 may have, for example, an octagon, hexagon, star-shaped or cross-section of other shape in a view perpendicular to the longitudinal axis of the passage 18, so long as the largest cylindrical body that can be received in the passage 18 has a diameter no greater than about 0.5 cm, and preferably no greater than about 0.1 cm.

The radius of chamfer forming the entrance 22 is at least two times the effective diameter of the passage 18. Preferably, the radius of the chamfer forming the entrance 22 is at least 0.2 cm, more preferably is at least 0.21, cm and most preferably is 0.23 cm or greater. The apparatus 10 is rectangular and therefore does not roll if unintentionally dropped. The apparatus 10 is small enough to comfortably fit within the hand; preferred overall dimensions of the apparatus 10 are 2.5 cm×2.5 cm×1.2 cm.

The end 20 is spaced from the top 24 an appropriate distance to limit insertion of the syringe tip. For syringe tips of smaller lengths (e.g., 1.0 to 2.5 cm), the distance between the end 20 and the top 24 is preferably about ½ the length of the syringe tip. If the syringe tip has a longer length (e.g., 3.0 to 7.5 cm), the distance between the end 20 and the top 24 is preferably one-third to one-fourth the overall length of the syringe tip. However, in certain applications it is advantageous to extend the passage 18 completely through the body 16 and avoid an internal closed end so that dust, contaminants or other debris that otherwise might collect in the passage 18 will instead descend through the body 16 and out of the passage 18.

FIG. 3a illustrates an assembly 25 that includes the apparatus 10 and a disposable syringe 26. The syringe 26 has a barrel 28 containing a quantity of fluid to be dispensed such as dental etching gel. The lower end of the barrel 28 is connected to a neck 30 that, in turn, is coupled to a formable, tubular, stainless steel syringe tip 32.

Although not shown, the syringe 26 also includes a thumb-operated plunger having a head slidably received in the barrel 28. The plunger with its head is movable along a longitudinal axis 34 (FIG. 3a) of the barrel 28 in order to urge fluid in the barrel 28 through a relatively small passage in the tip 32 and toward an application site. An example of a syringe is a 3 cc Burron syringe (P3-O-L Syringe Assembly, Burron Medical Inc.) or its equivalent.

The syringe tip 32 has an outer cylindrical wall that initially extends in a straight line along the axis 34. In order to bend the tip 32 to a desired curved orientation, the tip 32 is advanced into the passage 18 until the furthermost end of the tip 32 contacts the end 20 of the passage 18. Next, the syringe 26 is moved in an arc from the position shown in FIG. 3a to the position shown in FIG. 3b as the apparatus 10 remains stationary in order to deform the material of the tip 32 past its yield point and cause the tip 32 to thereafter have the configuration shown in FIG. 3b.

The chamfered entrance 22 provides a gradual forming surface that facilitates bending the tip 32 in a smooth curve to avoid the likelihood of kinking the tip 32 or otherwise unduly restricting the narrow passage within the tip 32. Advantageously, the tip 32 can be readily observed during the bending procedure, enabling the user to ensure that the ultimate configuration of the tip 32 closely approximates the desired configuration. The maximum angle that the outer portion of the tip 32 can be bent relative to the longitudinal axis 34 of the barrel 28 is normally limited by contact of the neck 30 or the barrel 28 with the top 24 of the substrate 12; in this regard, an angular configuration approaching 5 to 85 degrees can normally be attained with conventional syringes. However, an angle in the range of 30 to 60 degrees is sufficient for many applications.

FIG. 4 illustrates another embodiment of the invention wherein a dental mixing well 110 includes a substrate 112 formed with at least two mixing or dispensing recesses 113. Although not shown, three recesses 113 are preferably provided for mixing and/or dispensing three different dental materials, along with an opaque cover for optionally closing one or more recesses 113 in order to inhibit premature drying or curing of materials contained within the recesses 113.

A top 124 of the substrate 112 is convex and includes a raised portion 125 that lies above the level of the top 124 surrounding the recesses 113. A passage 118 and an entrance 122, essentially identical to passage 18 and entrance 22 illustrated in FIGS. 1-3, are connected to the raised portion 125. The passage 118 descends in a direction approximately perpendicular to the adjacent overlying section of the raised portion 125.

Figure 5:
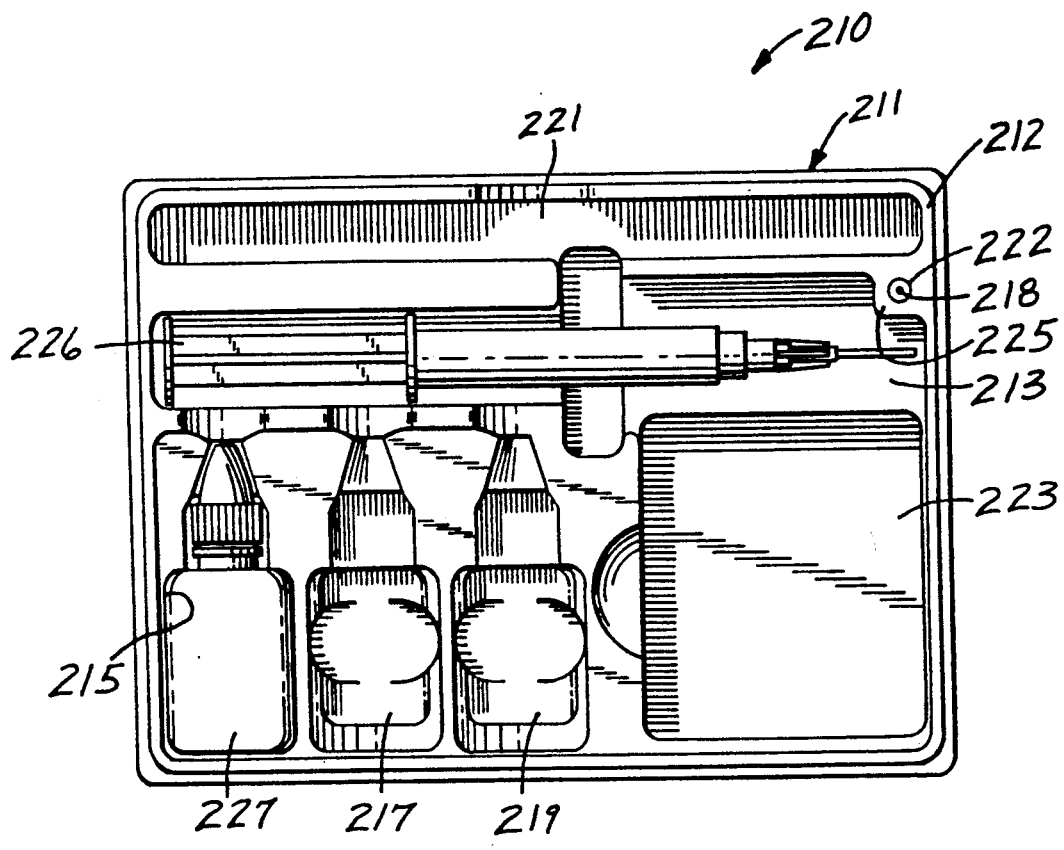
FIG. 5 is a plan view of another embodiment of the invention, wherein a package includes a substrate with a passage for forming a syringe tip.

FIG. 5 depicts another embodiment of the invention, wherein an assembly 210 includes a package 211 having a vacuum-formed substrate 212. The substrate 212 includes a first elongated recess 213 and a second recess 215. A syringe 226 is removably received in the first recess 213, and a container of dental material 227 is received in the second recess 215. The shape of the recess 215 is complemental to the overall configuration of the container 227.

The substrate 212 also includes a third and fourth recess 217, 219 for receiving containers of other types of dental material. In addition, a fifth recess 221 is provided to receive one or more brushes for applying the dental material. A sixth recess 223 is adapted to receive a pad of disposable paper sheets for mixing or dispensing dental preparations. The sixth recess 223 may also receive a mixing well similar to well 110 illustrated in FIG. 4.

An upper portion 225 of the substrate 212 is reinforced and lies at an elevation equal to the elevation of a raised wall separating the first recess 213 from the fifth recess 221. The upper portion 225 includes a vertical passage 218 and an upwardly opening chamfered entrance 222 essentially identical to the passage 18 and entrance 22 shown in FIGS. 1-3.

Figure 6:
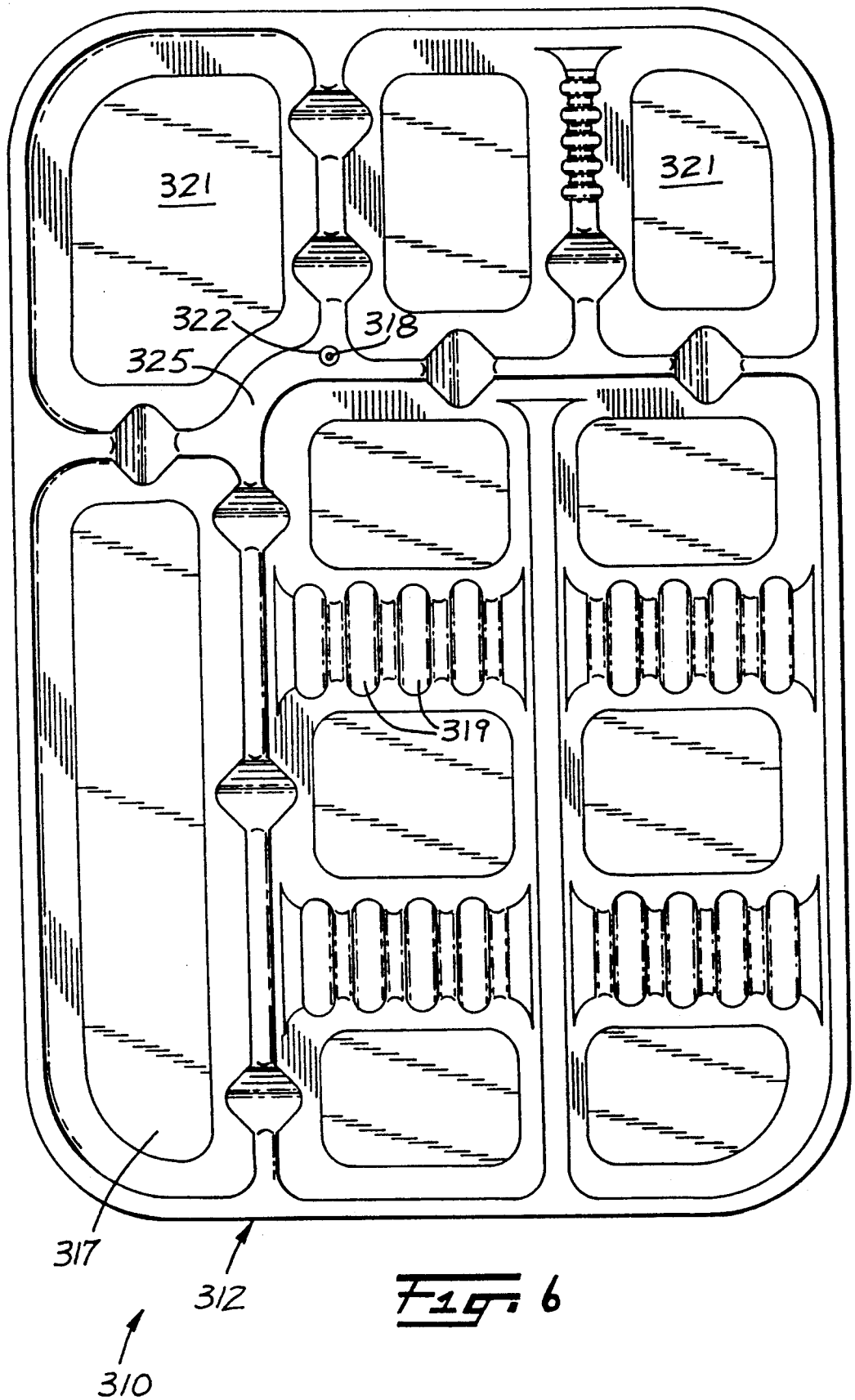
FIG. 6 is a plan view of yet another embodiment of the invention, wherein a dental instrument setup tray includes a passage for bending a syringe tip.

Another embodiment of the invention is shown in FIG. 6, wherein a dental instrument setup tray 310 comprises a substrate 312 preferably made of stainless steel or relatively hard, sterilizable plastic. The substrate 312 has a bottom 317 and a plurality of raised, spaced apart holders 319 above the bottom 317. The holders 319 have channels for supporting dental instruments at a position spaced above the bottom 317. The substrate 312 also has a number of recesses 321 for containing other instruments, containers of dental materials or other items as the practitioner may choose.

An upper portion 325 of the tray substrate 312 is spaced above the bottom 317 and includes a vertical passage 318 and an upwardly opening chamfered entrance 322 essentially identical to the passage 18 and entrance 22 shown in FIGS. 1-3. If the substrate 312 has sufficient weight, a syringe tip such as tip 32 may be formed within the passage 318 and entrance 322 without the need for grasping the tray 310.

The embodiments shown in FIGS. 4-6 are advantageous in that a separate tool is unnecessary and the forming apparatus is conveniently at hand. Further, in the case of apparatus such as mixing well 110 and tray 310, sterilization of the apparatus simultaneously sterilizes the passage and chamfered entrance.

Figure 7:
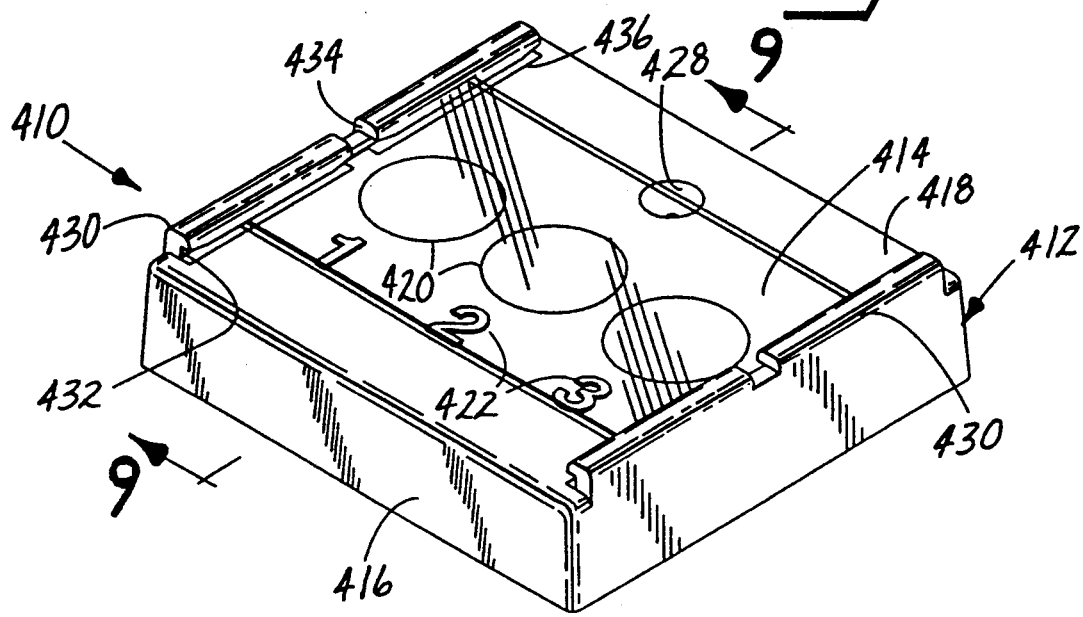
FIG. 7 is a perspective view of a dental dispensing tray constructed according to a currently preferred embodiment of the invention.
Figure 8:
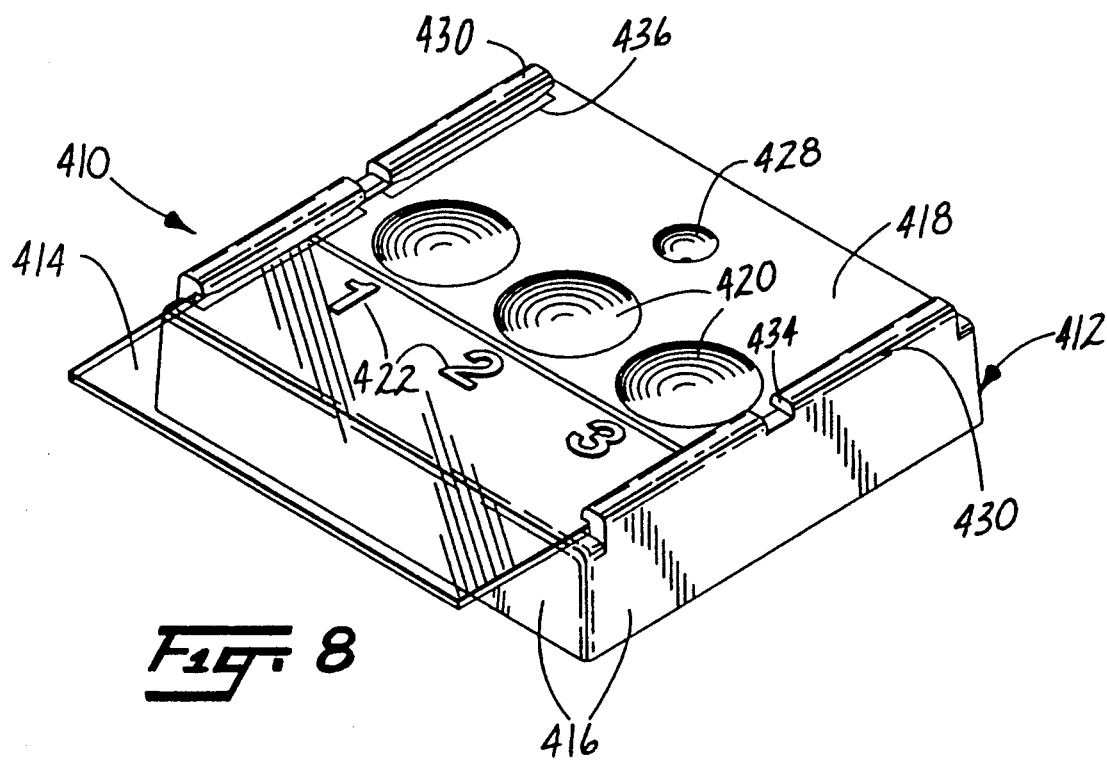
FIG. 8 is a perspective view somewhat similar to FIG. 7 except that a cover of the tray is shown in an open orientation.
Figure 9:
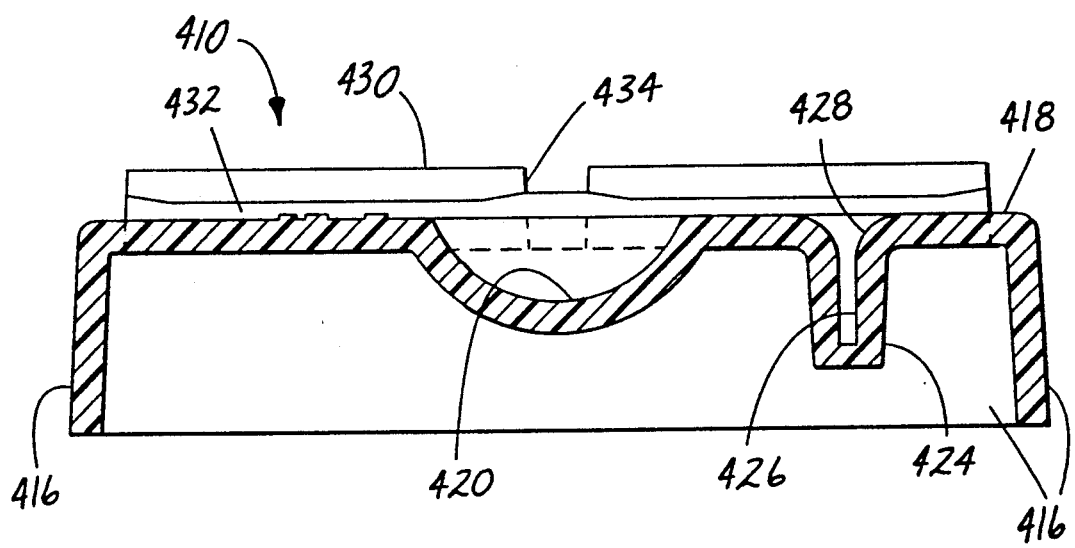
FIG. 9 is an enlarged cross-sectional view of the tray shown in FIGS. 7-8 taken along lines 9—9 of FIG. 7, except that the cover has been removed.

A currently preferred embodiment of the invention is illustrated in FIGS. 7–9, wherein a dispensing tray 410 that is also described in co-pending U.S. patent application Ser. No. 07/978,117 filed on even date herewith. The tray includes a base substrate 412 and a cover 414 (FIGS. 7–8 only). The substrate 412 includes four upright walls 416 that are integrally connected at their upper edges to a horizontally-extending platform 418 having an overall rectangular shape.

The platform 418 is connected to three side-by-side mixing wells 420 aligned along a central axis of the platform 418 in its elongated direction. The mixing wells 420 have a smoothly curved configuration similar to a partial sphere and unbroken by recesses, grooves and the like, and are adapted to contain a quantity of dental material that is curable upon exposure to actinic radiation. As can be observed in FIG. 7, the wells 420 are identified by numerical indicia 422 to assist the user in remembering which type of material is in a particular well 420.

A depending, somewhat cylindrical body 424 (FIG. 9) is integrally connected to the platform 418, and includes an elongated vertical passage 426 that is essentially cylindrical, but preferably has a slight frustoconical taper in the range of 1 to 2 degrees to facilitate molding. A trumpeted or chamfered entrance 428 is connected to the passage 426, and as shown in FIG. 9 provides a smoothly curved transition between the passage 426 and a top of the platform 418. The arc forming the entrance 428 is tangential at its uppermost end with the top of the platform 418, and is tangential at its lowermost end with the inner wall of the body 424 defining the passage 426.

Preferably, the passage 426 has a diameter in the range of 0.8 mm to 0.9 mm, and the radius forming the entrance 428 is 2.3 mm. The lower end of the passage 426 is spaced from the top of the platform 418 a distance of 6.3 mm to limit insertion of the syringe tip. The passage 426 together with the entrance 428 is useful for bending the tip of a dispensing syringe.

A pair of elongated, upstanding bars 430 are integrally connected to the platform 418 along the shorter two of the four walls 416. The bars 430 include inwardly directed flanges that present opposed grooves 432. Each of the bars 430 has a central, upper notch 434 that extends through the respective flanges. As shown for example in FIG. 9, the flanges have a tapered lead-in next to the grooves 432 along their outer ends as well as in areas adjacent the notches 434.

The cover 414 has an overall rectangular configuration with slightly rounded corners, and the shorter pair of edges of the cover 414 are received in the grooves 432 for sliding movement therealong. The thickness of the cover 414 is 0.76 mm, while the height of the grooves 432 is 0.86 mm in order to facilitate sliding of the cover 414 in smooth fashion. Rectangular cutouts 436 in the platform 418 are disposed below overhanging portions of the flanges of the bars 430 as illustrated in FIG. 7–8.

The overall dimensions of the substrate 412 are sufficiently small (for example, 5.2 cm×4.8 cm×1.3 cm) such that the entire substrate 412 comfortably fits within the confines of one hand. The underside of the substrate 412 is open, and the bottom of the wells 420 and the inner surfaces of the walls 416 provide finger-gripping structure for the fingers of one hand to hold and also to steady movement of the tray 410 while the thumb of the same hand is placed atop the cover 414 for manipulating movement of the cover 414 relative to the substrate 412. If desired, ridges, recesses or other types of frictional thumb-engaging structure may be provided on the top of the cover 414 to enhance engagement of the thumb with the cover 414 during sliding motion.

The grooves 432 together with the notches 434 provide structure for enhancing smooth sliding motion of the cover 414 relative to the substrate 412, so that dental materials such as liquids having a relatively low viscosity are not spilled or otherwise dislodged from the wells 420 as the cover 414 is moved from its first, closed orientation that is illustrated in FIG. 7 and to a second, open orientation that is illustrated in FIG. 8. The second orientation is spaced from the first orientation a sufficient distance to uncover the wells 420. The notches 434 provide stress relief for the bars 430 when the walls 416 are inadvertently squeezed together, so that the bars 430 do not unduly bind against the edges of the cover 414 and hinder movement of the latter.

The substrate 412 and the bars 430 are integrally molded of black polypropylene that is opaque to light in the visible spectrum including actinic radiation that might otherwise prematurely begin to cure material in the wells 420. On the other hand, the cover 414 is made from a sheet of poly(ethylene glycol-co-cyclohexane-1,4-dimethanol terephthalate) ("PETG") that includes sufficient colorant (preferably, an orange colorant) to prevent transmission of a substantial portion of actinic radiation, and yet transmit at least part of the visible light spectrum so that dental material in the wells 420 can be observed when the cover 414 is in its closed position. Other suitable materials for the cover 414 are described in U.S. Pat. No. 4,978,007, the disclosure of which is incorporated by reference herein.

The bars 430, including the grooves 432, comprise a means for slidably coupling the cover 414 to the substrate 412 in order to enable the cover to smoothly move between an open and a closed orientation. Importantly, the tray 410 lacks any snap-action latch such as molded dimples, recesses or protrusions for releasably retaining the cover 414 in a closed or an open position, as such structure might otherwise cause the tray 410 to be sufficiently jolted during movement of the cover 414 to cause material in the wells 420 to be spilled or otherwise dislodged. The thickness of the cover 414 is sufficiently large to preclude the cover 414 from freely falling from the grooves 432 when the tray 410 is tilted.

The width of the cover 414 (i.e., the shorter of the two dimensions along the plane of the cover 414) relative to the width of the substrate 412 is sufficiently small to enable a portion of the cover 414 to project past the adjacent upright wall 416 of the substrate 412 when the cover 414 is moved to its open position as shown in FIG. 8. The projecting cover 414 when open is easy to engage by the fingers of the same hand that is holding the tray, so that return movement of the cover 414 to its closed position is facilitated.

What is claimed:
1. An assembly comprising:
   a syringe having a formable tip with a diameter less than about 0.5 cm; and
   a syringe tip forming apparatus including a substrate having a passage with an effective diameter no greater than about 0.5 cm, said substrate including a chamfered entrance connected to said passage, said chamfered entrance having a radius of at least two times the effective diameter.

2. The assembly of claim 1, wherein said passage is substantially cylindrical.

3. The assembly of claim 1, wherein said chamfered entrance has a radius of at least three times the effective diameter.

4. The assembly of claim 1, wherein said chamfered entrance has a radius of at least four times the effective diameter.

5. The assembly of claim 1, wherein said entrance and said passage together have an overall length of less than 2 cm.

6. A dental mixing well comprising a substrate having at least one recess for mixing or dispensing dental material, said substrate including an internal passage with an effective diameter no greater than about 0.5 cm for forming a syringe tip, said substrate including a chamfered entrance connected to said passage.

7. The well of claim 6, wherein said chamfered entrance has a radius of at least two times the effective diameter.

8. The well of claim 6, wherein said substrate includes a top having a raised portion, and wherein said entrance is located on said raised portion.

9. The well of claim 6, wherein said substrate has at least two recesses, a top, and a raised portion between said recesses, and wherein said entrance is located on said raised portion.

10. An assembly comprising:
a package having a first and second recess;
a container of dental material received in said first recess;
a syringe received in said second recess,
said package including a substrate having an internal passage with an effective diameter no greater than about 0.5 cm for forming a syringe tip, said substrate including a chamfered entrance connected to said passage.

11. The assembly of claim 10, wherein said chamfered entrance has a radius of at least two times the effective diameter.

12. The assembly of claim 10, wherein said substrate includes a raised portion above said second recess and wherein said entrance is located on said raised portion.

13. A dental instrument setup tray comprising a substrate having a bottom and a plurality of holders for holding dental instruments at a position spaced above said bottom, said substrate including an internal passage with an effective diameter no greater than about 0.5 cm for forming a syringe tip, said substrate including a chamfered entrance connected to said passage.

14. The tray of claim 13, wherein said entrance has a radius of at least two times the effective diameter.

15. The tray of claim 13, wherein said entrance is located at an elevation above said bottom.

16. The tray of claim 15, wherein said entrance is located at an elevation above said holders.

* * * * *